United States Patent
Hong et al.

(10) Patent No.: US 11,344,627 B2
(45) Date of Patent: May 31, 2022

(54) DENDRIMER-EXOSOME HYBRID NANOPARTICLES AS A DELIVERY PLATFORM

(71) Applicant: WISCONSIN ALUMNI RESEARCH FOUNDATION, Madison, WI (US)

(72) Inventors: Seungpyo Hong, Madison, WI (US); Sin-Jung Park, Seoul (KR)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 152 days.

(21) Appl. No.: 16/011,992

(22) Filed: Jun. 19, 2018

(65) Prior Publication Data

US 2018/0369410 A1    Dec. 27, 2018

Related U.S. Application Data

(60) Provisional application No. 62/525,466, filed on Jun. 27, 2017.

(51) Int. Cl.

| | |
|---|---|
| *A61K 47/69* | (2017.01) |
| *A61K 49/18* | (2006.01) |
| *A61K 47/64* | (2017.01) |
| *A61K 31/519* | (2006.01) |
| *A61K 49/00* | (2006.01) |
| *A61K 47/59* | (2017.01) |
| *A61K 47/62* | (2017.01) |
| *A61K 9/50* | (2006.01) |
| *A61K 9/51* | (2006.01) |
| *A61K 38/00* | (2006.01) |
| *C07K 14/705* | (2006.01) |
| *C12N 5/0775* | (2010.01) |
| *C12N 5/09* | (2010.01) |
| *B82Y 5/00* | (2011.01) |

(52) U.S. Cl.
CPC ........ *A61K 47/6905* (2017.08); *A61K 9/5068* (2013.01); *A61K 9/5146* (2013.01); *A61K 31/519* (2013.01); *A61K 47/595* (2017.08); *A61K 47/62* (2017.08); *A61K 47/64* (2017.08); *A61K 47/6901* (2017.08); *A61K 47/6935* (2017.08); *A61K 49/0021* (2013.01); *A61K 49/0043* (2013.01); *A61K 49/0054* (2013.01); *A61K 49/0056* (2013.01); *A61K 49/0076* (2013.01); *A61K 49/0093* (2013.01); *A61K 49/0097* (2013.01); *A61K 49/1806* (2013.01); *A61K 49/1824* (2013.01); *C07K 14/7055* (2013.01); *C07K 14/70596* (2013.01); *C12N 5/0662* (2013.01); *C12N 5/0663* (2013.01); *C12N 5/0693* (2013.01); *A61K 38/00* (2013.01); *B82Y 5/00* (2013.01); *C12N 2509/00* (2013.01); *C12N 2533/30* (2013.01)

(58) Field of Classification Search
None
See application file for complete search history.

(56) References Cited

U.S. PATENT DOCUMENTS

2010/0160299 A1 *  6/2010  Baker, Jr ............. A61K 47/595
                                                                        514/221

FOREIGN PATENT DOCUMENTS

WO    WO-2015084677 A1 *  6/2015
WO    WO-2018107061 A1 *  6/2018  ............. C12N 15/87

OTHER PUBLICATIONS

Yeo, R.W.Y., et al., "Mesenchymal stem cell: An efficient mass producer of exosomes fordrug delivery", Adv. Druf. Deliv. Rev., pp. 336-341 (Year: 2013).*
Ma, P., et al., "Targeted delivery of polyamidoamine-paclitaxel epidermal growth factor receptor 2 trastuzumab", Int. J. Nanomed., pp. 2173-2190 (Year: 2015).*
Hazawa, M., et al., "Radiation increases the cellular uptake of exosomes through CD29/CD81 complex formation", Biochem. Biophysc. Res. Comm., pp. 1165-1171 (Year: 2016).*
Li, J., et al., "Thrombin-activated platelet-derived exosomes regulate endothelial cellexpression of ICAM-1 via microRNA-223 during thethrombosis-inflammation response", Thrombosis Res., pp. 96-105 (Year: 2017).*
Charoenviriyakul, C., et al., "Cell type-specific and common characteristics of exosomes derived frommouse cell lines: Yield, physicochemical properties,and pharmacokinetics", Eur. J. Pharm. Sci., pp. 316-322 (Year: 2016).*
Feng, Y., et al. "Identification of exosomal and non-exosomal microRNAs associated with the drug resistance of ovarian cancer", Molec. Med. Rep., pp. 3376-3392 (Year: 2019).*
Peinado, Héctor et al. "Melanoma exosomes educate bone marrow progenitor cells toward a pro-metastatic phenotype through MET." Nature medicine vol. 18,6: 883-91. doi:10.1038/nm.2753 (Year: 2012).*
Lai et al.; "Exomsomes for Drug Delivery—a Novel Application for the Mesenchymal Stem Cell"; Biotechnology Advances; 31; pp. 543-551; (2013).
Sunoqrot et al.; "In Vitro Evaluation of Dendrimer-Polymer Hybrid Nanoparticles on Their Controlled Cellular Targeting Kinetics"; Molecular Pharmaceutics; 10; pp. 2157-2166; (2013).
Sunoqrot et al.; "Kinetically Controlled Cellular Interactions of Polymer-Polymer and Polymer-Liposome Nanohybric Systems"; Bioconjugate Chemistry; 22; pp. 466-474; (2011).

(Continued)

*Primary Examiner* — Michael G. Hartley
*Assistant Examiner* — Lance W Rider
(74) *Attorney, Agent, or Firm* — Cantor Colburn LLP

(57) ABSTRACT

Described herein are hybrid nanoparticles that are exosomes loaded with one or more nanoparticle dendrimers. Also included are pharmaceutical compositions including the hybrid nanoparticles and methods of making the hybrid nanoparticles. Also described is a method of treating a human subject by administering to the human subject the above-described hybrid nanoparticles.

9 Claims, 10 Drawing Sheets
(10 of 10 Drawing Sheet(s) Filed in Color)
Specification includes a Sequence Listing.

(56) References Cited

OTHER PUBLICATIONS

Sunoqrot et al.; "Prolonged Blood Circulation and Enhanced Tumor Accumulation of Folate-Targeted Dendrimer-Polymer Hybrid Nanoparticles"; Journal of Controlled Release; 191; pp. 115-122; (2014).
Sunoqrot et al.; "Temporal Control Over Cellular Targeting Through Hybridization of Folate-Targeted Dendrimers and PEG-PLA Nanoparticles"; Biomacromolecules; 13; pp. 1223-1230; (2012).
Jiang et al.; "Eradication of Acute Myeloid Leukemia with FLT3 Ligand-Targeted miR-150 Nanoparticles"; Cancer Res; 76(15); 11 pages; Aug. 1, 2016, doi: 10.1158/0008-5472.CAN-15-2949.
Jiang et al.; "miR-22 Has a Potent Anti-tumour role with Therapeutic Potential in Acute Myeloid Leukaemia"; Nature Communications, Published Apr. 26, 2016; 15 pages; DOI: 10/1038/ncomms11452.
Park et al.; "A Novel Exosome-Dendrimer-Magnetic Nanoparticle Hyrid System for Cancer Cell Targeting"; a Poster presented at the 2017 UW-Madison School of Pharmacy Research Day on Feb. 10, 2017.

\* cited by examiner

SEQUENCE LISTING

```
<160> NUMBER OF SEQ ID NOS: 4

<210> SEQ ID NO 1
<211> LENGTH: 13
<212> TYPE: PRT
<213> ORGANISM: Homo sapiens

<400> SEQUENCE: 1

Met Leu Tyr Asn Pro Thr Thr Tyr Gln Met Asp Val Asn
1               5                   10

<210> SEQ ID NO 2
<211> LENGTH: 13
<212> TYPE: PRT
<213> ORGANISM: Homo sapiens

<400> SEQUENCE: 2

Val Thr Tyr Asn Thr Asp Thr Phe Glu Ser Met Pro Asn
1               5                   10

<210> SEQ ID NO 3
<211> LENGTH: 14
<212> TYPE: PRT
<213> ORGANISM: Homo sapiens

<400> SEQUENCE: 3

Met Tyr Trp Gly Asp Ser His Trp Leu Gln Tyr Trp Tyr Glu
1               5                   10

<210> SEQ ID NO 4
<211> LENGTH: 27
<212> TYPE: PRT
<213> ORGANISM: Homo sapiens

<400> SEQUENCE: 4

Asn Lys Phe Asn Lys Gly Met Arg Gly Tyr Trp Gly Ala Leu Gly Gly
1               5                   10                  15

Gly Asn Gly Lys Arg Gly Ile Arg Gly Tyr Asp
            20                  25
```

DENDRIMER-EXOSOME HYBRID NANOPARTICLES AS A DELIVERY PLATFORM

CROSS-REFERENCE TO RELATED APPLICATIONS

This application claims priority to U.S. Provisional Application 62/525,466 filed on Jun. 27, 2017, which is incorporated herein by reference in its entirety.

FIELD OF THE DISCLOSURE

The present disclosure is related to nanocarriers for therapeutic agents, particularly cancer therapeutics.

BACKGROUND

There is an urgent need for the development of cancer therapeutics, and in particular means for cancer cell-specific targeting using nanocarriers which can provide enhanced therapeutic indices with reduced side effects. One of the promising approaches in nanocarrier design is to hybridize two (or more) different types of nanocarriers into a single platform. For example, 50-200 nm nanoparticles (NPs) can exploit the tumor characteristic enhanced permeability and retention (EPR) effect, relatively longer plasma circulating time, and biodistribution to liver and spleen. In contrast, smaller nanoparticles (below 10 nm) can provide efficient cell uptake, tumor penetration and diffusion, and biodistribution to the kidneys. It has previously been reported that hybrid nanoparticles (NPs) combining poly(amidoamine) (PAMAM) dendrimers and poly(D,L-lactic acid)-co-poly (ethylene glycol) (PLAPEG) copolymers can provide a combination of the biological behaviors of such NPs in a single platform in a controlled manner. This approach, however, still does not address the potential issues of immunogenicity and long-term toxicity of artificial nanomaterials.

To address potential toxicity issue and to achieve long-circulating NP systems, there has been a growing interest in creating and engineering biomimetic nanoparticles that combine nanoparticles with cell membranes. This approach allows efficient biological interfacing that provides a potential opportunity to treat highly complex diseases, such as cancer. Previous efforts include hybrid NPs that integrate various NPs, including poly(lactideco-glycolide) (PLGA) NPs and gold NPs, with plasma membranes from red blood cells (RBCs), platelets, and cancer cells. This design is particularly promising for personalized medicine allowing engineered nanocarriers coated with cell membranes from the patient's own cells. Furthermore, RBC-camouflaged NPs reportedly achieved a significant increase in plasma circulation from 15.8 hours to 39.6 hours in terms of elimination half-life, supporting the potential of this approach. Despite the promising results, current challenges include the limited drug loading of the core PLGA NPs (typically in a range of 1-5%) and impaired tissue penetration due to the inherent limitation in size that is approximately 100 nm.

What is needed are additional approaches for biomimetic nanoparticles for delivery of therapeutic agents.

BRIEF SUMMARY

In one aspect, a hybrid nanoparticle comprises an exosome loaded with one or more nanoparticle dendrimers.

In another aspect, a pharmaceutical composition comprises the foregoing hybrid nanoparticle.

In another aspect, a method of making hybrid nanoparticles comprises
isolating a stem cell or tumor cell from a subject,
expanding the stem cell or tumor cell to provide an expanded cell population,
culturing the expanded cell population,
isolating exosomes from the expanded cell population,
removing the internal components of the isolated exosomes to provide ghost exosomes, and
contacting the ghost exosomes with dendrimer nanoparticles under conditions suitable for uptake of the dendrimer nanoparticles into the ghost exosomes to provide the hybrid nanoparticles.

In yet another aspect, a method of treating a human subject comprises administering to the human subject the above-described hybrid nanoparticles.

BRIEF DESCRIPTION OF THE DRAWINGS

The patent or application file contains at least one drawing executed in color. Copies of this patent or patent application publication with color drawings will be provided by the Office upon receipt and payment of the necessary fee (37 CFR § 1.17(h)) as Small Entity.

The above-described and other features will be appreciated and understood by those skilled in the art from the following detailed description, drawings, and appended claims.

DETAILED DESCRIPTION

Figure 1:
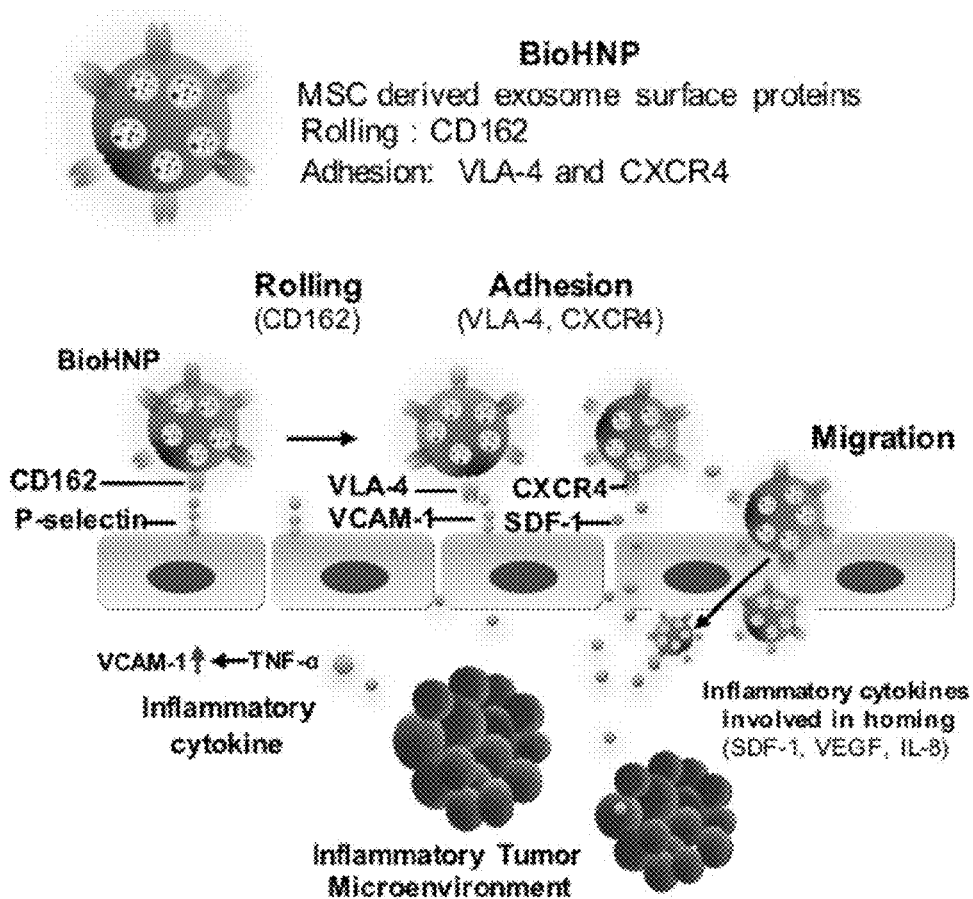
FIG. 1 is a schematic of the proposed targeting mechanism of biomimetic exosome-dendrimer hybrid nanoparticles.

The inventors have developed biomimetic exosome-dendrimer hybrid nanoparticles, or BioHNPs. This design has a number of potential advantages, which has the potential to be transformative in designing new nanocarriers. Without being held to theory, the anticipated targeting mechanisms that this design will exploit are illustrated in FIG. 1. First, as the dendrimers are protected by exosomal membranes, the nanocarriers are expected to evade immune detection and clearance by the reticuloendothelial system (RES), resulting in prolonged circulation in the body. Second, expressed markers from hMSC, such as CD162, VLA-4, and CXCR4, will mediate interactions with angiogenic, inflamed endothelia via a series of interactions involving rolling (P-selectin) and firm adhesion (VCAM-1 and SDF-1), respectively, resulting in efficient extravasation to reach the cancerous tissue. Note that tumor necrosis factor-α (TNF-α) secreted from the inflammatory tumor microenvironment induces the increase expression of VCAM-1 and P-selectin that respectively bind to VLA-4 and CD162 expressed by exosomes. All of these interactions, along with the inflammatory cytokines, such as SDF-1, VEGF, and IL-8, will allow the facilitated transmigration of exosomes across the endothelial layers. Third, drug molecules will be covalently associated with surface engineered PAMAM dendrimers that have shown their great efficiency in mediating strong multivalent binding effect for improved targeting efficacy and highly efficient tumor penetration and diffusion owing to their small size (2-5 nm in diameter) and flexibility/deformability. These dendrimer characteristics are expected to allow drug molecules to be delivered to effectively target and kill cancer cells including those in the deep core of solid tumors. Combined, the multi-step targeting mechanisms, involving long circulation, rolling/adhesion/migration, and improved targeting and penetration, have great potential to provide a novel drug delivery system.

Human mesenchymal stem cells (hMSCs) are nonhematopoietic adult stem cells with multilineage potential. hMSCs are defined by plastic adherence, differentiation potential, and cell surface marker expression. An emerging body of literature shows that hMSCs exhibit tropism for sites of the tumor microenvironment, attracted by inflammatory mediators (cytokines, chemokines, and other potential chemoattractant molecules) secreted by cancerous regions, posing their potential as novel drug delivery systems. However, using the whole cells as drug carriers has a number of issues, including the difficulty in removing all intracellular components, size control, and complicated purification steps. Meanwhile, it has been recently found that the vast majority of the surface properties (including protein/marker expression) of parent cells remains unchanged on the surface of exosomes. Exosomes are non-immunogenic and are in a size of 25-100 nm that is ideal for taking advantage of the enhanced permeability and retention (EPR) effect. Exosomes are generally known to circulate long in the systemic circulation, due to their good tolerance in the body as evidenced by their wide distribution in biological fluids such as blood, urine, and breast milk. As a result, it has been reported that various exosomes carry drug/gene molecules and exhibit targeting to angiogenic endothelia in the case of hMSC-derived exosomes. Nonetheless, issues with exosomes to be used as sole drug carriers include undesired delivery of intra-exosomal components, limited targeting efficacy, and limited possible choice of drugs and genetic materials affected by their physical properties such as charge, size, and hydrophobicity. The hybrid nanoparticles described herein address at least some of these issues.

In an embodiment, a hybrid nanoparticle comprises an exosome loaded with one or more nanoparticle dendrimers. As used herein, exosome refers to small vesicles having a membrane structure that are secreted from various cells. Exosomes have diameters of about 25 to about 150 nm. Fusion between plasma membranes and multivesicular bodies occurs, which releases the exosomes to the outside of the cells. Exosomes function in long-distance intercellular communication. Exosomes typically exhibit prolonged circulation half-lives, high tolerance in biological fluids, and the same membrane characteristics as their parent cells. These unique features of exosomes can be exploited when used as outer layers of a nanocarrier system.

Exosomes may express markers such as VLA-4, CD162, CXCR4, CD9, CD63, CD81 or a combination thereof.

In an embodiment, the exosome is derived from a stem cell or a tumor cell which is isolated from a subject, e.g., a human subject.

Stem cells include embryonic stem cells or adult stem cells, preferably, adult stem cells. The adult stem cells may be, without being limited to, mesenchymal stem cells, human tissue-derived mesenchymal stromal cells (mesenchymal stromal cell), human tissue-derived mesenchymal stem cells, multipotent stem cells, or amniotic epithelial cells, preferably, mesenchymal stem cells. The mesenchymal stem cells may be derived from, without being limited to, the umbilical cord, umbilical cord blood, bone marrow, fat, muscle, nerve, skin, amnion, placenta, and the like.

In an embodiment, the stem cell is a mesenchymal stem cell. Mesenchymal stem cells (MSCs) can specifically target inflammatory regions that are frequently found in cancerous regions, i.e., MSC tumor-homing.

In another embodiment, the exosome is isolated from a tumor cell. Tumor cells actively produce, release, and utilize exosomes to promote tumor growth.

Exosomes can be produced by isolating tumor or stem cells from a subject, expanding the tumor or stem cells to provide an expanded cell population, culturing the expanded cell population, and isolating the exosome secreted from the expanded tumor or stem cells. The internal components can be removed from the isolated exosomes to provide so-called ghost exosomes which are essentially empty vessels for loading components such as nanoparticle dendrimers. Exosomes derived from a patient can provide a non-immunogenic nanocarrier shell to the patient, in addition to the features above, allowing an option for personalized medicine.

The term "dendrimer" as used herein includes, but is not limited to, a molecular architecture with an interior core, interior layers (or "generations") of repeating units regularly attached to and extending from this initiator core, each layer having one or more branching points, and an exterior surface of terminal groups attached to the outermost generation. Dendrimers have regular dendrimeric or "starburst" molecular structures. Nanoparticle dendrimers generally have diameters of 3 to 10 nm, which is particularly useful for the penetration of tumor tissue.

Each successive dendrimer generation can be covalently bound to the previous generation. The number of reactive groups of the core structure determines n-directionality and defines the number of structures that can be attached to form the next generation.

The number of branches in a dendritic structure is dependent on the branching valency of the monomeric building blocks, including the core. For example, if the core is a primary amine, the amine nitrogen would then be divalent, resulting in a 1-2 branching motif.

Exemplary dendrimers are alkylated dendrimers such as poly(amido-amine) (PAMAM), poly(ethyleneimine) (PEI), polypropyleneimine (PPI), diaminobutane amine polypropylenimine tetramine (DAB-Am 4), polypropylamine (POPAM), polylysine, polyester, iptycene, aliphatic poly(ether), aromatic polyether dendrimers, or a combination comprising one or more of the foregoing.

The dendrimers can have carboxylic, amine and hydroxyl terminations and can be of any generation including, but not limited to, generation 1 dendrimers (G1), generation 2 dendrimers (G2), generation 3 dendrimers (G3), generation 4 dendrimers (G4), generation 5 dendrimers (G5), generation 6 dendrimers (G6), generation 7 dendrimers (G7), generation 8 dendrimers (G8), generation 9 dendrimers (G9), or generation 10 dendrimers (G10). Hybrid nanoparticles can also be formed from generations of dendrimers greater than 10.

The PAMAM dendrimers contain internal amide bonds which may enhance their biodegradability, thus improving tolerance in terms of human therapeutic applications. The surface includes polar, highly reactive primary amine groups. The surfaces of the amino-functional PAMAM dendrimers are cationic and can be derivatized, either through ionic interactions with negatively charged molecules, or using many well-known reagents for covalent functionalization of primary amines.

When PAMAM dendrimers are employed, generations from 0 to 7 PAMAM dendrimers are typically used. For example, hybrid nanoparticles can be formed from generation 0 PAMAM dendrimers (G0); generation 1 (G1) PAMAM dendrimers; generation 2 (G2) PAMAM dendrimers; generation 3 (G3) PAMAM dendrimers; generation 4 (G4) PAMAM dendrimers; generation 5 (G5) PAMAM dendrimers; generation 6 (G6) PAMAM dendrimers; or generation 7 (G7) PAMAM dendrimers. PAMAM is commercially available from multiple sources, including Sigma-Aldrich (Cat. No. 597309).

Diaminobutane amine polypropylenimine tetramine (DAB Am 4) is a polymer with a 1,4-diaminobutane core (4-carbon core) with 4 surface primary amino groups. When hybrid nanoparticles are formed from DAB-AM 4 dendrimers, generations from 0 to 7 DAB-AM 4 dendrimers are typically used. For example, hybrid nanoparticles can be formed from generation 0 DAB-AM 4 dendrimers (G0); generation 1 (G1) DAB-AM 4 dendrimers; generation 2 (G2) DAB-AM 4 dendrimers; generation 3 (G3) DAB-AM 4 dendrimers; generation 4 (G4) DAB-AM 4 dendrimers; generation 5 (G5) DAB-AM 4 dendrimers; generation 6 (G6) DAB-AM 4 dendrimers; or generation 7 (G7) DAB-AM 4 dendrimers. DAB-Am 4 is commercially available from multiple sources, including Sigma-Aldrich (Cat. No. 460699).

The hybrid nanoparticles may be formed of one or more different dendrimers. Each dendrimer of the dendrimer complex may be of similar or different chemical nature than the other dendrimers (e.g., the first dendrimer can be a PAMAM dendrimer, while the second dendrimer can in be a POPAM dendrimer). In some embodiments, the first or second dendrimer may further include an additional agent. The dendrimer complex can include multiple dendrimers. For example, the nanoparticle can include a third dendrimer; wherein the third-dendrimer is complexed with at least one other dendrimer. A third agent can be complexed with the third dendrimer. In another embodiment, the first and second dendrimers are each complexed to a third dendrimer, wherein the first and second dendrimers are PAMAM dendrimers and the third dendrimer is a POPAM dendrimer. Additional dendrimers can be incorporated. When multiple dendrimers are utilized, multiple agents can also be incorporated.

In one aspect, dendrimers are modified by reaction with alkyl epoxides, wherein the R group of the epoxide has 1 to 30 carbon atoms. In some embodiments, the alkyl epoxides react with amino groups present on the dendrimers to form an alkylated dendrimer.

The amine groups present on the dendrimers provide reactive sites for a variety of amine-based conjugation reactions using coupling linkers that include, but are not limited to, dicyclohexylcarbodiimide, diisopropylcarbodiimide, N-(3-Dimethylaminopropyl)-N'-ethylcarbodiimide, 1,1'-carbonyldiimidazole, N-succinimidyl S-acetylthioacetate, N-succinimidyl-S-acetylthiopropionate, 2-Mercaptoethylamine, sulfosuccinimidyl 4-(N-maleimidomethyl)cyclohexane-1-carboxylate, succinimidyl iodoacetate, succinimidyl 3-(2-pyridyldithio)propionate. In some embodiements, reactive esters are used to link dendrimers and other compounds via ester bonds. Examples of the reactive esters include, but are not limted to, N-hydroxysuccinimide ester, N-hydroxy sulfosuccinimide ester, N-γ-maleimidobutyryl-oxysulfosuccinimide ester, nitrophenyl ester, tetrafluoro phenyl ester, pentafluorophenyl ester, a thiopyridyl ester a thionitrophenyl ester. Preferably, the reactive ester group is an N-hydroxysuccinimide ester.

The large number of end groups on the dendrimer allows for conjugation of a wide variety of molecules. The dendrimer is associated with, e.g., complexed or conjugated with, one or more of a therapeutic, targeting, prophylactic or diagnostic agent. Diagnostic agents include imaging agents.

In one aspect, the therapeutic agent is a chemotherapeutic agent. Chemotherapeutic agents include, but are not limited to, the following classes: alkylating agents, antimetabolites, anthracyclines, plant alkaloids, topoisomerase inhibitors, monoclonal antibodies, and other anti-tumor agents. In addition to the chemotherapeutic drugs described above, namely doxorubicin, paclitaxel, other suitable chemotherapy drugs include tyrosine kinase inhibitor imatinib mesylate (Gleeve® or Glivec®), cisplatin, carboplatin, oxaliplatin, mechloethamine, cyclophosphamide, chlorambucil, azathioprine, mercaptopurine, pyrimidine, vincristine, vinblastine, vinorelbine, vindesine, podophyllotoxin (L01CB), etoposide, docetaxel, topoisomerase inhibitors (L01CB and L01XX) irinotecan, topotecan, amsacrine, etoposide, etoposide phosphate, teniposide, dactinomycin, lonidamine, and monoclonal antibodies, such as trastuzumab (Herceptin®), cetuximab, bevacizumab and rituximab (Rituxan®), among others.

Other examples of therapeutic agents include, but are not limited to, antimicrobial agents, analgesics, anti-inflammatory agents, and others. Antibiotics can be incorporated into the particle, such as vancomycin, which is frequently used to treat infections, including those due to methicillin resistant staph aureus (MRSA). The particle optionally includes cyclosporin, a lipophilic drug that is an immunosuppressant agent, widely used post-allogeneic organ transplant to reduce the activity of the patient's immune system and the risk of organ rejection (marketed by Novartis under the brand names Sandimmune® and Neoral®). Particles comprising cyclosporine can be used in topical emulsions for treating keratoconjunctivitis sicca, as well. In this regard, particles with multifunctional surface domains incorporating such drugs can be designed to deliver equivalent dosages of the various drugs directly to the cancer cells, thus potentially minimizing the amount delivered generally to the patient and minimizing collateral damage to other tissues.

Therapeutic agents also include therapeutic nucleic acids such as gene-silencing agents, gene-regulating agents, antisense agents, peptide nucleic acid agents, ribozyme agents, RNA agents, and DNA agents. Nucleic acid therapeutic agents include single stranded or double-stranded RNA or DNA, specifically RNA, such as triplex oligonucleotides, ribozymes, aptamers, small interfering RNA including siRNA (short interfering RNA) and shRNA (short hairpin RNA), antisense RNA, microRNAs (miRNAs), or a portion thereof, or an analog or mimetic thereof, that is capable of reducing or inhibiting the expression of a target gene or sequence. Inhibitory nucleic acids can act by, for example, mediating the degradation or inhibiting the translation of mRNAs which are complementary to the interfering RNA sequence.

Engineering of the dendrimer surfaces with targeting ligands allows strong binding to target cells via multivalent binding effect (avidity effect), providing an additional level of specificity. Targeting agents direct the dendrimer to a specific biological location. Non-limiting examples of targeting ligands include drugs, vaccines, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, DNA, cDNA, antisense constructs, ribozymes, and the like). Targeting agents are useful for delivery of the functionalized nanoparticle to specific cell types and/or organs, as well as sub-cellular locations.

Extracellular matrix targeting agents include, but are not limited to, heparin binding moieties, matrix metalloproteinase binding moieties, lysyl oxidase binding domains, negatively charged moieties or positively charged moieties and hyaluronic acid. Functional transport moieties include, but are not limited to, blood brain barrier transport moieties, intracellular transport moieties, organelle transport moieties, epithelial transport domains and tumor targeting moieties (folate, other), GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, HDL ligands, and aptamers.

In an aspect, the targeting agent is a tumor-targeting peptide. Tumor-targeting peptides are specific for tumor-related surface markers and can be used to deliver therapeutic agents to a tumor. Tumor-targeting peptides can be specific for specific types of cancer cells.

Diagnostic agents are agents that enable the detection or imaging of a tissue or disease. Examples of diagnostic agents include, but are not limited to, radiolabels, fluorophores and dyes.

Imaging agent refers to a label that is attached to the random copolymer of the present invention for imaging a tumor, organ, or tissue in a subject. Examples of imaging agents include, without limitation, radionuclides, fluorophores such as fluorescein, rhodamine, Texas Red, Cy2, Cy3, Cy5, and the AlexaFluor® (Invitrogen, Carlsbad, Calif.) range of fluorophores, antibodies, gadolinium, gold, nanomaterials, horseradish peroxidase, alkaline phosphatase, derivatives thereof, and mixtures thereof.

Radiolabel refers to a nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance.

Administration of a prophylactic agent can occur prior to the manifestation of symptoms characteristic of the disease or disorder, such that the disease or disorder is prevented or, alternatively, delayed in its progression.

Therapeutic molecules, targeting agents, imaging agents, and genetic agents may be combined with dendrimers via chemical conjugation, physical encapsulation, and/or electrostatic interaction methods.

Also included are pharmaceutical compositions comprising the hybrid nanoparticles.

As used herein, "pharmaceutical composition" means therapeutically effective amounts of the compound together with a pharmaceutically acceptable excipient, such as diluents, preservatives, solubilizers, emulsifiers, and adjuvants. As used herein "pharmaceutically acceptable excipients" are well known to those skilled in the art.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations well known in the art. Topical administration includes transdermal formulations such as patches.

For topical application to the eye, the inhibitor may be made up into a solution or suspension in a suitable sterile aqueous or non-aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anesthetics, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

In an aspect, a method of making hybrid nanoparticles comprises isolating a stem cell or tumor cell from a subject, expanding the stem cell or tumor cell to provide an expanded cell population, culturing the expanded cell population, isolating exosomes from the expanded cell population, removing the internal components of the isolated exosomes to provide ghost exosomes, contacting the ghost exosomes with dendrimer nanoparticles under conditions suitable for uptake of the dendrimer nanoparticles into the ghost exosomes to provide the hybrid nanoparticles. In an aspect, the conditions suitable for uptake of the dendrimer nanoparticles into the either exosomes or ghost exosomes comprise sonication, treatment of hypotonic medium, electroporation, heat shock, or a combination thereof.

In another embodiment, a method of treating a human subject comprises administering to the subject a hybrid nanoparticle as described herein. Exemplary human subjects include cancer patients. In an aspect, the exosomes are isolated from a tumor from the patient or stem cells from the patient, and the dendrimer includes at least one chemotherapeutic agent.

The compositions and methods described herein are applicable to all cancers including solid tumor cancers, e.g., those of the breast, prostate, ovaries, lungs and brain, and liquid cancers such as leukemias and lymphomas.

The methods described herein can be further combined with additional cancer therapies such as radiation therapy, chemotherapy, surgery, and combinations thereof.

The invention is further illustrated by the following non-limiting examples.

EXAMPLES

Methods

Cell line and cell culture: Human mesenchymal stem cells (hMSCs) (Lonza, Allendale, N.J.) were cultured in minimum essential medium/Alpha modification medium (MEM-alpha) with 20% fetal bovine serum (FBS) and penicillin (100 unit/mL)-streptomycin (100 μg/mL). The cells were maintained in a humidified incubator with 5% $CO_2$ at 37° C.

Purification of hMSC-derived exosomes: hMSC-derived exosomes were collected by sequential centrifugation from hMSCs as previously described. Briefly, the culture medium was removed and replaced with exosome-deficient medium (MEM-α with 1% bovine serum albumin) for 24 hrs. The conditioned medium was then collected and spun down at 300×g for 10 min to remove the remaining cells. To remove cell debris and large extracellular vesicles, the conditioned medium was spun at 20,000×g for 30 min. The supernatant was then concentrated using an Amicon® centrifugal filter device (MWCO 10,000 Da), followed by additional centrifugation at 100,000×g at 4° C. for 2 hrs. The pellet containing exosomes was washed with PBS and centrifuged at 100,000×g at 4° C. for 2 hrs. The final exosome pellet was resuspended in 200 μL of PBS and its protein concentration was measured using a bicinchoninic acid assay (BCA assay; Pierce, Waltham, Mass.).

Dendrimer modification: Synthesis of Rhodamine (Rho)-labeled PAMAM dendrimers-PAMAM dendrimers, generation 4 (G4) (10 mg, 0.7 μmol) were dissolved in 1 mL phosphate buffered saline (PBS). A solution of NHS-Rho (1.1 mg, 2.1 μmol) in 1 mL PBS was added dropwise to the dendrimer solution and then the reaction mixture was stirred at room temperature overnight. The product was purified using an Amicon® centrifugal filter device (MWCO 3000 Da).

Acetylation of Rho-labeled G4 dendrimers (G4-Ac)—The Rho-labeled G4 dendrimers (G4-Ac) were acetylated as described earlier. Briefly, Rho-labeled G4 dendrimers (10 mg, 0.6 μmol) were dissolved in 1 mL methanol and reacted with acetic anhydride (33 mg, 324 μmol) and triethanolamine (58 mg, 389 μmol) for 24 hr at room temperature. The resulting solution was purified using a centrifugal filter device (MWCO 3000 Da).

Synthesis of folic acid (FA)-targeted G4 dendrimers (G4-FA)—Rho-labeled G4 dendrimers (10 mg, 0.6 μmol) were dissolved in 1 mL DMSO and incubated with EDC (0.1 mg, 0.8 μmol) and NHS (0.1 mg, 1.1 μmol) for 1 hr at room temperature. The solution was then reacted with a solution of FA in DMSO (1.1 mg, 2.5 μmol) for 24 hr at room temperature. The product was purified using a centrifugal filter device (MWCO 3000 Da). To minimize non-specific binding of the dendrimer with cells, the product was fully acetylated as previously described and the final product (G4-FA) was purified using a centrifugal filter device (MWCO 3000 Da).

Preparation of dendrimer-exosome hybrid nanoparticles (NPs): To prepare dendrimer-loaded exosomes, dendrimers (80 μg of protein) and exosomes (20 μg of protein) were mixed in 1 mL PBS and the mixture was sonicated using a bath sonicator (40% amplitude, 10 cycles, and 20 s on/off). The resulting solution was incubated at 37° C. for 1 hr. The solution was then spun at 100,000×g at 4° C. for 2 hrs in order to remove unloaded dendrimers. The pellet (dendrimer-loaded exosomes) was then resuspended in PBS.

Characterization of the hMSC-derived exosomes and the dendrimer-exosome hybrid NPs: To measure the size of the hMSC-derived exosomes, the exosomes in PBS at a concentration of 5 μg of protein/mL were prepared and further diluted 1000-fold and the diluted solution was then analyzed using the NanoSight LM10 (Malvern Instruments, Massachusetts, Mass.).

The zeta potential was measured using the Zetasizer ZS (Malvern Instruments, Massachusetts, Mass.) at a concentration of 5 μg of protein/mL.

Identification of key membrane proteins on the exosomes with and without dendrimer loading was assessed using the western blot. Briefly, the hMSC-derived exosomes and the dendrimer-loaded exosomes were lysed in RIPA buffer. The proteins were separated using a 10% SDS-PAGE gel and then blotted onto a PVDF membrane. The proteins on the membrane were blocked using a solution containing 5% BSA in PBS-T for 30 min, then incubated with primary antibodies at 4° C. overnight. The membrane was subsequently incubated with HRP-conjugated secondary antibodies at room temperature for 1 hr. The membrane was then washed, incubated with a substrate solution, and visualized using a Gel Documentation system (BioRad, Hercules, Calif.).

Immunostaining: To determine P-selectin and VCAM-1 expression on endothelial cells upon TNF-α-treatment, HUVEC cells were cultured on a cover glass and treated with 20 ng/mL of TNF-α at 37° C. for 4 hrs. The cells were fixed with 4% paraformaldehyde and blocked using a 5% BSA solution in PBS for 30 min. The cells were then incubated with primary antibodies against P-selectin or VCAM-1 for 1 hr at room temperature. The cells were incubated with fluorescence-labeled secondary antibodies for 1 hr at room temperature. The cells were washed, mounted with a mounting medium, and observed using a confocal microscope (Zeiss, Dublin, Calif.).

Selective binding and uptake of the hybrid NPs to HUVEC cells under the static and under the flow conditions: To test the selective binding and uptake of the dendrimer-exosome hybrid NPs in the static condition, HUVEC cells were cultured on a cover glass and treated with or without TNF-α for 4 hrs prior to incubation of the hybrid NPs. The cells were then treated with 20 μg of protein/mL for 2 hr at 37° C. The cells were harvested with trypsin and the fluorescence intensities from the cells were measured using Flow cytometry (BD, Franklin Lakes, N.J.). The mean fluorescence intensity (MFI)-fold changes were obtained by normalizing to the MFI from the TNF-α-untreated cells.

The cell association studies under the flow condition were conducted by infusing exosomes into a rectangular flow chamber. Briefly, HUVEC cells were cultured on a slide glass until a confluent cellular monolayer was formed. The cells were treated with TNF-α for 4 hr prior to the experiment and then the cell-slide was placed in the flow chamber. Exosomes (200 μg of protein) or control vesicles (200 μg, liposomes composed of 1,2-Dioleoyl-sn-glycero-3-phosphocholine, 1,2-dioleoyl-sn-glycero-3-phosphoethanolamine-PEG2000, and cholesterol) were dispersed in 1 mL culture medium and injected into the flow chamber for 40 min at 25 μL/min. The cell-surface was washed using PBS for 10 min at 50 μL/min. The cells were harvested and analyzed using the flow cytometry as described previously.

In vitro analysis of cell binding and uptake of the dendrimer-exosome hybrid NPs using tumor cells: The binding and uptake of the hybrid NPs were tested using two tumor cell lines (human colorectal adenocarcinoma cell line, HT29 and human breast adenocarcinoma cell line, MCF-7). Briefly, the cells were cultured on a cover glass and treated with TNF-α (20 ng/mL) for 4 hr at 37° C. prior to treat the hybrid NPs. The cells were then treated with 20 μg of protein/mL for 2 hr at 37° C. TNF-α-untreated cells were used as a control and all the cells were mounted and harvested for confocal and flow cytometry analysis, respectively. The MFI-fold changes were obtained as described previously.

Cell interaction of the dendrimer-exosome hybrid NPs at various incubation hours: To test the cellular interaction of the hybrid NPs and dendrimers released from the NPs over incubation time, the hybrid NPs were pre-incubated in PBS at 37° C. for 0, 24, and 48 hr to allow the dendrimers to be released from the exosomes. KB cells were cultured in folate-depleted medium at least for 14 days to induce the overexpression of folate receptors. The KB FR+ cells were then seeded on a cover glass and treated with the hybrid NPs for 2 hr with and without TNF-α-pretreatment. The cells were washed with PBS, mounted, and observed using a fluorescence microscopy (Zeiss, Dublin, Calif.).

Example 1

Characterization of the Dendrimer-Magnetic Nanoparticle (MNP) Conjugate (DMNP)

Figure 2:
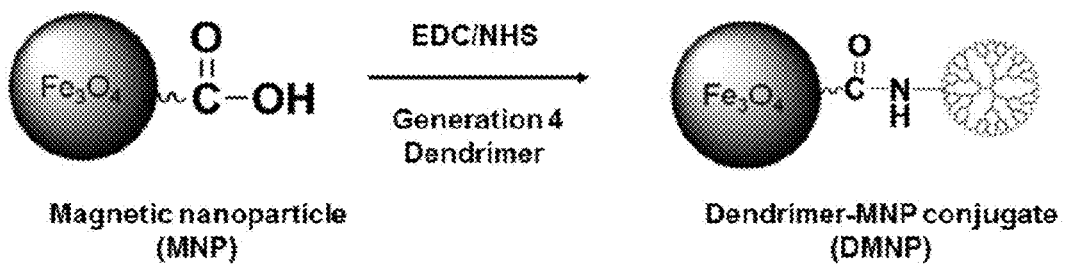
FIG. 2 shows a schematic of generation 4 (G4) PAMAM dendrimers conjugated to magnetic nanoparticles (MNP) with carboxylate end groups via the EDC/NHS coupling method to provide dendrimer-MNP conjugates (DMNP).
Figure 3:
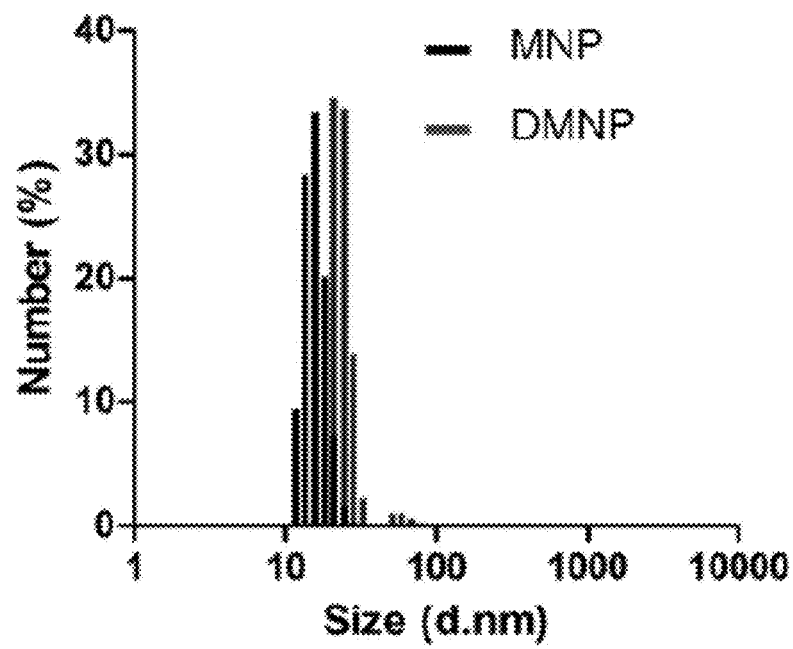
FIG. 3 shows the MNP and DMNP were 18 and 35 nm in diameter, respectively, as measured by Malvern Zetasizer.
Figure 4:
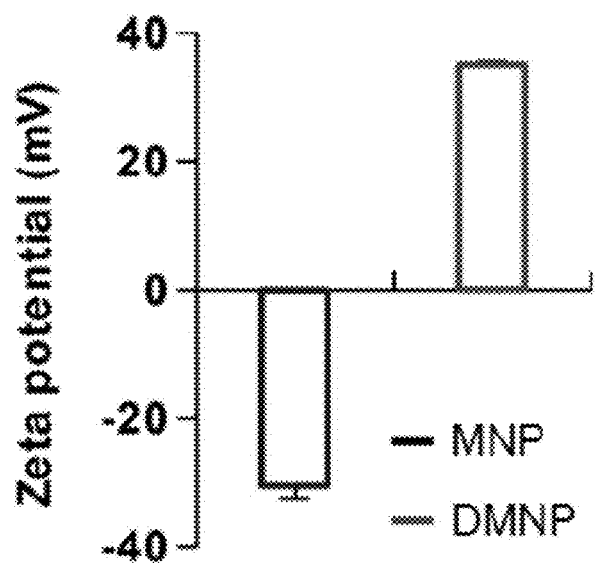
FIG. 4 shows the successful conjugation of the dendrimers to the magnetic nanoparticle was determined by change in surface change of the MNP from negative to positive.

Generation 4 (G4) PAMAM dendrimers were conjugated to magnetic nanoparticles with carboxylate end groups via the EDC/NHS coupling method as shown in FIG. 2. The MNP and DMNP were 18 and 35 nm in diameter, respectively, as measured by the Malvern Zetasizer and shown in FIG. 3. The successful conjugation of the dendrimers to the magnetic nanoparticle was determined by change in surface change of the MNP from negative to positive and is shown in FIG. 4.

Example 2

Isolation and Characterization of hMSC-Derived Exosomes

Figure 5:
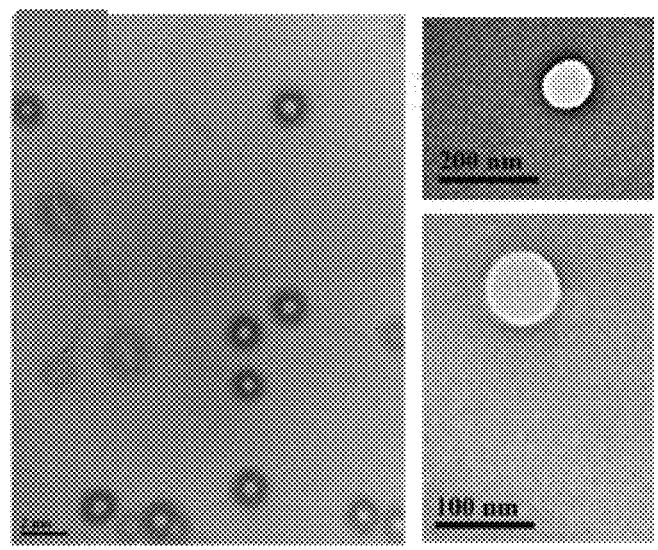
FIG. 5 shows TEM micrographs of Human Mesenchymal Stem Cell (hMSC)-derived exosomes.
Figure 6:
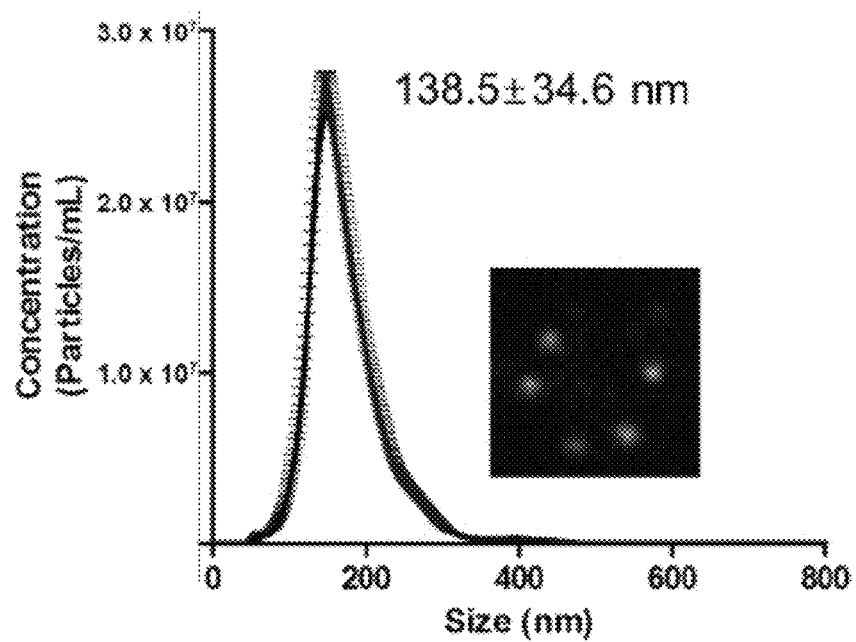
FIG. 6 shows nanoparticle tracking analysis (NTA) results of collected exosomes (inset: image of the exosomes taken during the NTA measurements).
Figure 7:
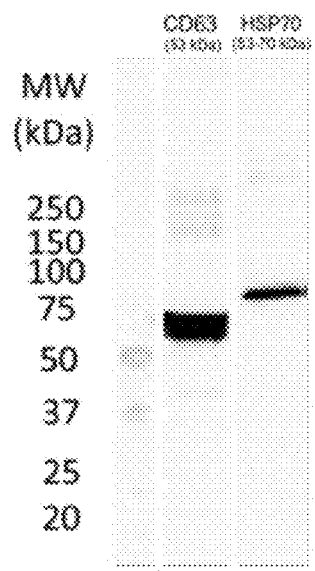
FIG. 7 is a Western blot of the exosomes, showing their expression of CD63 and HSP70.

Exosomes were isolated from hMSC following procedures known in the art. Briefly, hMSCs were placed into an exosome-free medium 24 hrs before the experiment. The medium containing exosomes secreted from hMSCs was collected and spun down at 100,000×g for 2 hrs, which was repeated twice. The resulting pellets were then re-suspended in PBS and stored at 80° C. before use. The resulting exosomes were characterized using TEM and a nanoparticle tracking analyzer (NTA) as shown in FIGS. 5 and 6. The size of the exosomes was measured to be approximately 100 nm using TEM and 140 nm using NTA. The protein expression of the hMSC derived exosomes was also examined. FIG. 7 shows that the exosomes express both CD63 and HSP70 (commonly used exosome markers). Collectively, these data indicate that exosomes can be successfully isolated from hMSCs and carry the characteristic exosome markers.

Example 3

Potential Selectivity of hMSC-Derived Exosomes to Activated HUVEC Cells

Figure 8:
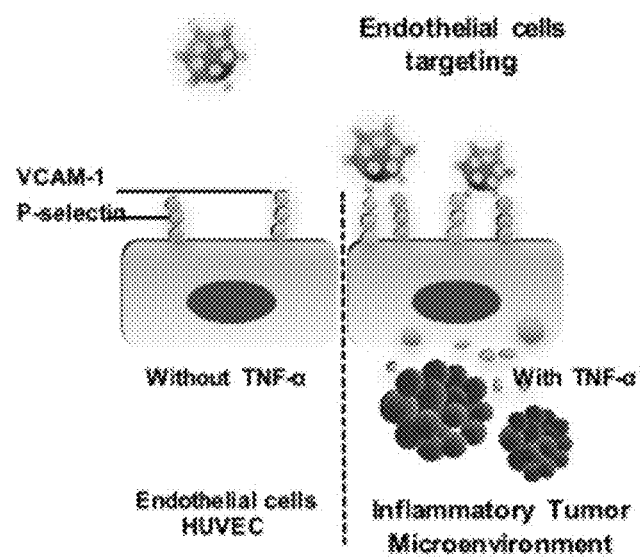
FIG. 8 is a schematic diagram of hMSC exosomes exhibiting hMSC-like homing to inflammatory tumor microenvironment.
Figure 9:
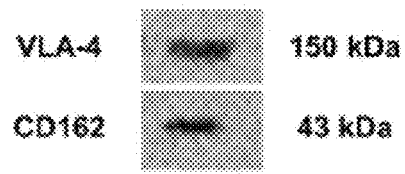
FIG. 9 is a Western blot of exosomes showing their expression of VLA-4 and CD162.
Figure 10:
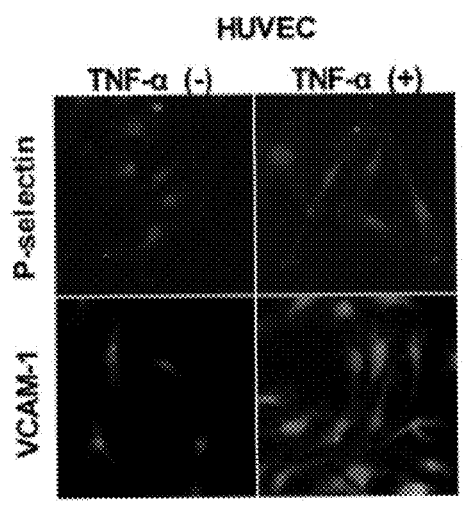
FIG. 10 shows increased expression levels of P-selectin and VCAM-1 from HUVEC cells upon TNF-α.

Potential advantages of using hMSC-derived exosomes would include the utilization of the homing properties of hMSCs to inflamed endothelia that are frequently found in cancerous regions. FIG. 8 is a schematic of hMSC exosomes inhibiting hMSC-like homing to the inflammatory tumor microenvironment. Human umbilical vein endothelial cells (HUVEC) were used to determine if the exosomes could potentially interact with the cells upon activation using TNF-α. TNF-α is known to induce expression of vascular cell adhesion molecule-1 (VCAM-1) and P-selectin that are directly involved in the hMSC binding to endothelial layers. The expression of VLA-4 and CD162 that are ligands binding to VCAM-1 and P-selectin, respectively, from the exosomes was confirmed using western blotting (FIG. 9). The confocal images shown in FIG. 10 revealed that the HUVEC cells overexpress P-selectin (red) and VCAM-1

(green) upon TNF-α treatment, indicating that this system will serve a good model for vascular targeting of hMSC-derived exosomes.

Example 4

In Vitro Targeting of hMSC Exosomes

Figure 11:
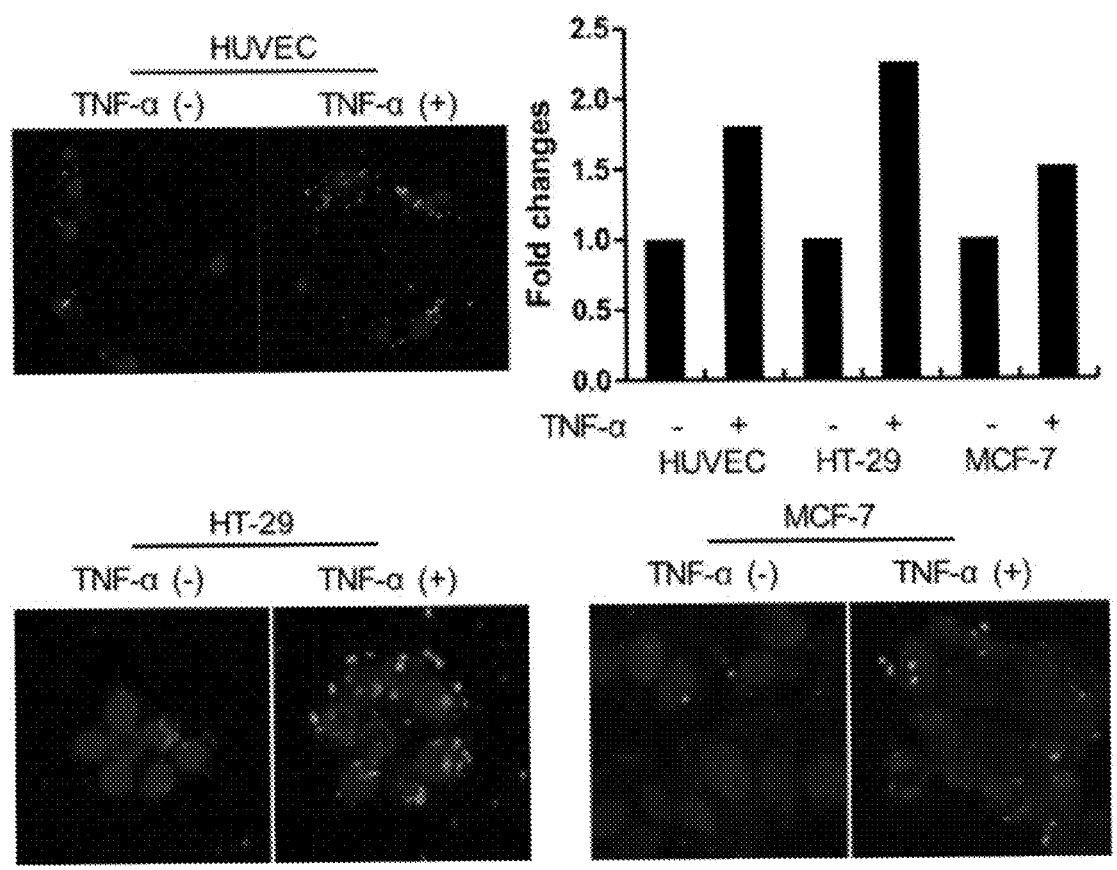
FIG. 11 shows in vitro targeting of hMSC-derived exosomes (green) to HUVEC, HT-29, and MCF-7 cells after treatment with TNF-α. The plot shows fold changes of fluorescence signals from the cells.

The selectivity of the hMSC-derived exosomes was then investigated using HUVEC, HT-29, and MCF-7 cells before and after TNF-α treatment. As shown in FIG. 11, the exosomes (green) strongly bound to all three cells after treated with TNF-α. Note that the exosomes were tagged with fluorescein isothiocyanate (FITC) prior to the incubation. The quantitative FACS results shown in the plot (upper right-hand corner) clearly indicate that exosomes selectively bound the three cell lines after activation using TNF-α.

Example 5

Loading of Exosomes on the Dendrimer-MNP Conjugate (DMNP)

Figure 12:
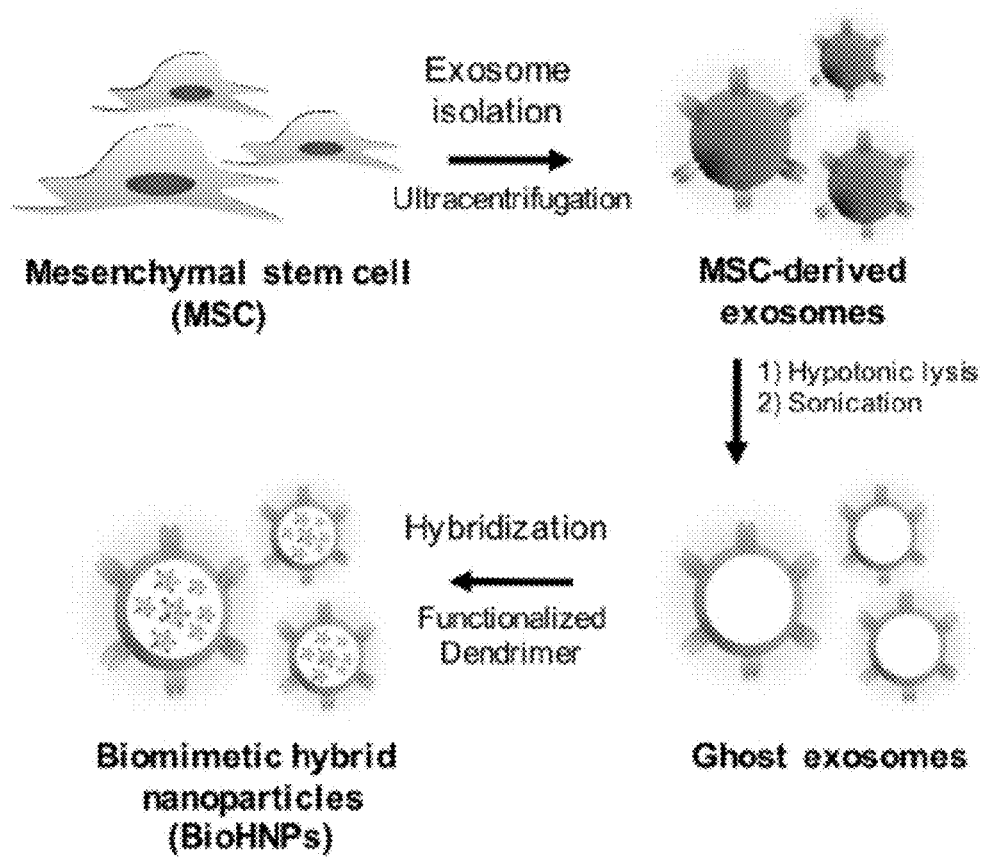
FIG. 12 is a schematic of biomimetic hybrid nanoparticle (BioHNP) preparation.

The overall hybridization process of BioHNPs is illustrated in FIG. 12. First, the hMSC-derived exosomes will go through hypotonic lysis and sonication to remove the internal components of the exosomes. To induce hypotonic lysis and release internal contents of exosomes, the exosomes will be re-suspended in a hypotonic medium consisting of 20 mM Tris-HCL (pH 7.5), 10 mM KCl, and 2 mM $MgCl_2$ in an ice bath for 20 min. The solution will be sonicated using a QSonica sonicator with 40% amplitude for 10 cycles of 20 sec on/off pulses on ice. To collect the empty exosomes, the solution will be centrifuged at 100,000×g for 2 h and the pellet will be re-suspended in water and stored at −80° C. before further use.

For dendrimer hybridization with the ghost exosomes, we will compare three methods: sonication, electroporation, and heat shock. Briefly, for the sonication methods, exosomes will be mixed with dendrimers in PBS and sonicated using QSonica sonicator with a 3.4 mm tip. The sonicator will be run at 40% amplitude for 10 cycles of 20 s on/off pulses on ice. After sonication, the exosome mixture will be incubated at 37° C. for one hr. For the electroporation method, exosome-dendrimer mixtures will be poured into a 4 mm electroporation cuvette and electroporated using a Bio-Rad Gene Pulser® II at 400 V and 125 μF capacitance for 12 ms followed by incubation at 37° C. for one hr. For the heat shock methods, exosome-dendrimer mixtures will be incubated in dry ice for 3 minutes and then immediately transferred to a 37° C. water bath for 3 min. This process will be repeated three times ending with incubation at 37° C. for one hr.

Each step of dendrimer functionalization, exosome separation and ghost formation, and hybridization will be thoroughly characterized. For dendrimer modification and conjugation, a series of analyses using 1H/13C NMR, UV/Vis, MALDI-TOF, Gel Permeation Chromatography (GPC), and High Performance Liquid Chromatography (HPLC) will be performed to quantitatively characterize the number of molecules attached and % conversion of the surface groups, along with their polydispersity. Sizes and morphologies of the resulting dendrimers, hMSC-derived exosomes, and BioHNPs will be observed using Dynamic Light Scattering (DLS), SEM, TEM, cryoTEM, and AFM.

Surface expression of various proteins will be checked using western blot assays. To confirm that hMSC-derived exosomes still exhibit the homing properties based on rolling and adhesion with endothelial layers, membrane proteins, such as CD162, VLA-4, CXCR4, that enable such interactions will be checked. Other general exosome markers, such as CD9, CD63, and CD81, will be assayed. Briefly, the hMSC-derived exosomes will be lysed using RIPA buffer containing a protease inhibitor cocktail. Fifty micrograms of total proteins will be separated on a 12% SDS-PAGE gel and transferred onto a PVDF membrane. The membrane will be blocked in 5% skim milk and incubated with a primary antibody at 4° C. overnight. Subsequently, a horseradish peroxidase (HRP)-conjugated secondary antibody will be used to amplify the signal. Protein signals will be detected using a Gel Doc image analysis system.

Various mixing ratios between dendrimers and ghost exosomes will be carefully tested to find an optimal condition for the highest efficiency. We will first calculate the dendrimer loading by monitoring the fluorescence signal intensities (from AF) or UV/Vis spectra (from AF and MTX). The level of conjugation and the mixing ratio will be selected at the level that achieves maximal efficiency without losing materials' well-controlled properties. In addition, the release kinetics of dendrimers from exosomes, along with the drug release profiles, will be measured.

DMNP loading into exosomes and loading efficiency were studied. The DMNP were loaded into exosomes using the sonication method. The exosome-DMNP hybrids were purified by passing them through a sephadex-100 column. The loading efficiency was >54%.

TABLE 1

| DMNP loading onto exosomes | | |
| --- | --- | --- |
| Target loading (%) | DMNP loading content (%) | Loading efficiency (%) |
| 5 | 3.02 ± 0.11 | 60.40 ± 2.26 |
| 10 | 4.80 ± 0.80 | 47.98 ± 8.05 |
| 20 | 12.80 ± 2.40 | 56.50 ± 6.36 |

Figure 13:
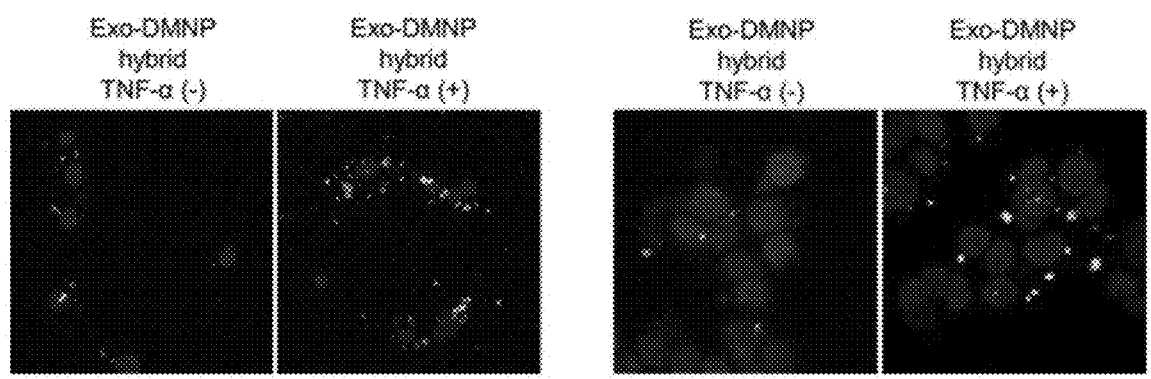
FIG. 13 shows in vitro analysis of cell binding and uptake of the dendrimer-exosome hybrid NPs using tumor cells.

Uptake of the hybrid nanoparticles into HUVEC and MCF-7 cells was studied. FIG. 13 shows confocal images of the cells (in presence and absence of induced inflammation) after exosome-DMNP hybrid nanoparticles treatment in the present and absence of TNF-α treatment. The results represent that the hybrid nanoparticles are selectively internalized into the inflamed cells.

Example 6

Selective Binding and Uptake of the Hybrid NPs Under the Flow Condition

The cell association studies under the flow condition were conducted by infusing exosomes into a rectangular flow chamber. Briefly, HUVEC cells were cultured on a glass slide until a confluent cellular monolayer was formed. The cells were treated with TNF-α for 4 hr prior to the experiment and then the cell-slide was placed in the flow chamber. Exosomes (200 μg of protein) or control vesicles (200 μg, liposomes composed of 1,2-Dioleoyl-sn-glycero-3-phosphocholine, 1,2-dioleoyl-sn-glycero-3-phosphoethanolamine-PEG2000, and cholesterol) were dispersed in 1 mL culture medium and injected into the flow chamber for 40 min at 25 μL/min. The cell-surface was washed using PBS for 10 min at 50 μL/min. The cells were harvested and analyzed using the flow cytometry as described previously.

Figure 14:
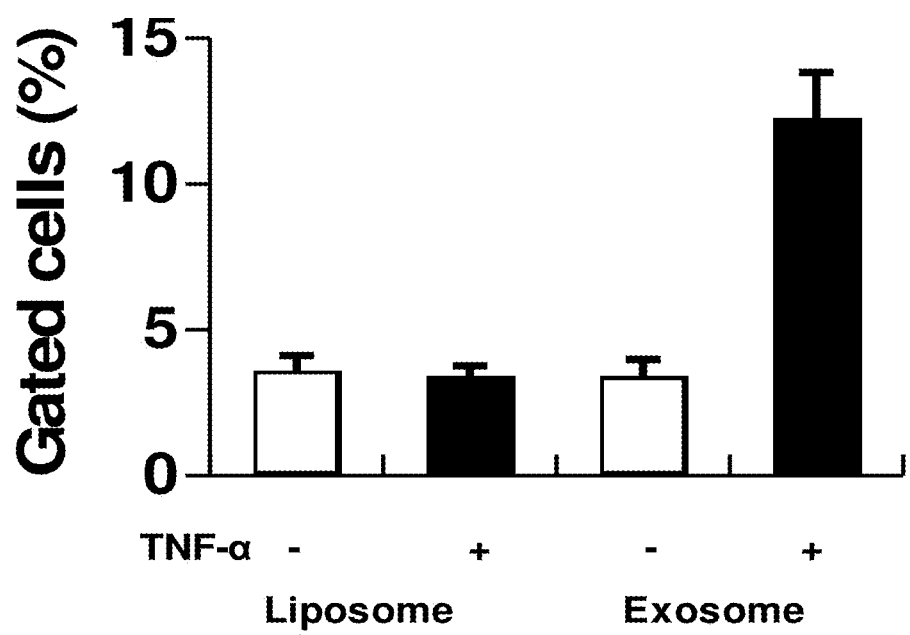
FIG. 14 shows cellular association of the exosomes and liposomes under the flow condition, measured using fluorescence activated cell sorting (FACS).

FIG. 14 shows the fluorescence intensities from HUVEC cells as a result of cellular association of hybrid NPs (exosome: FITC and G4-Ac: Rhodamine) were significantly increased after TNF-α treatment, and yet liposomes did not.

Example 7

Figure 15:
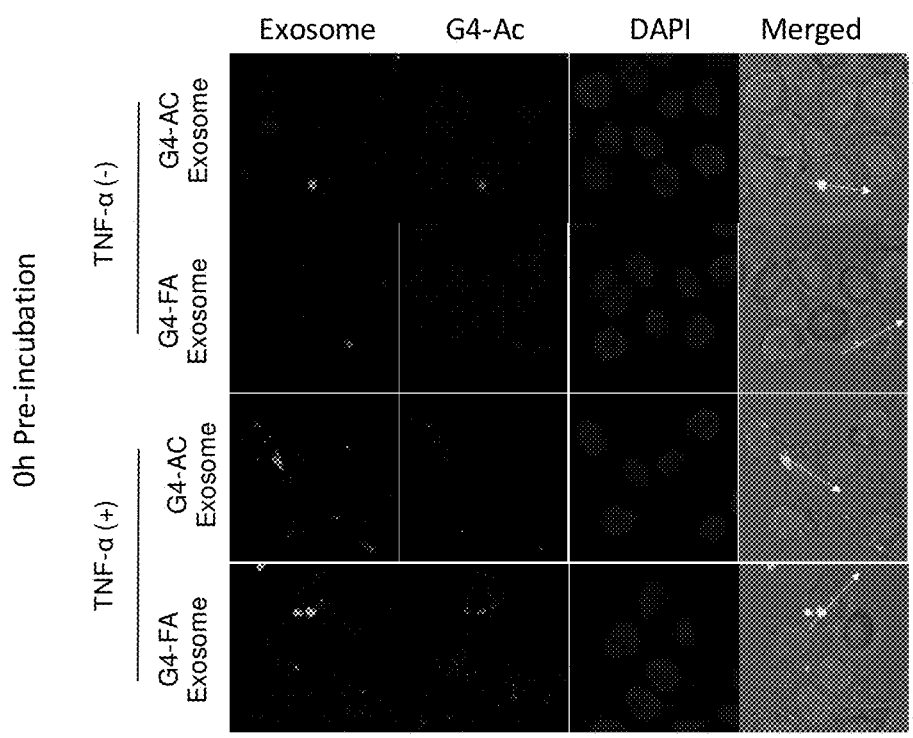
FIG. 15 shows cell interactions of the dendrimer-exosome hybrid NPs at 0 incubation hours.
Figure 16:
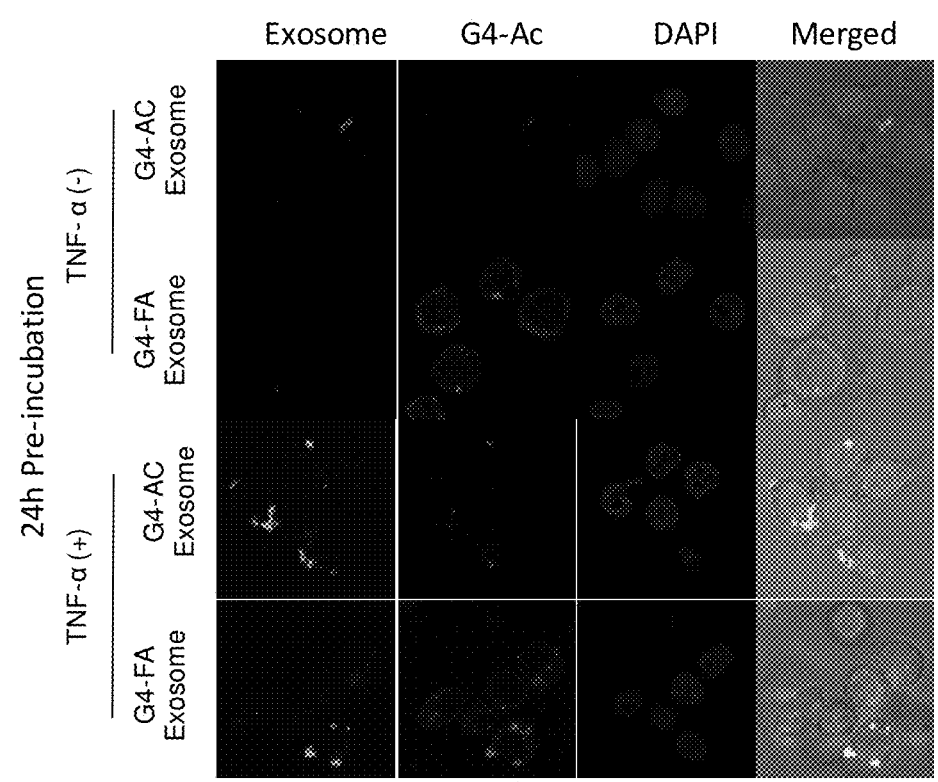
FIG. 16 shows cell interactions of the dendrimer-exosome hybrid NPs at 24 incubation hours.
Figure 17:
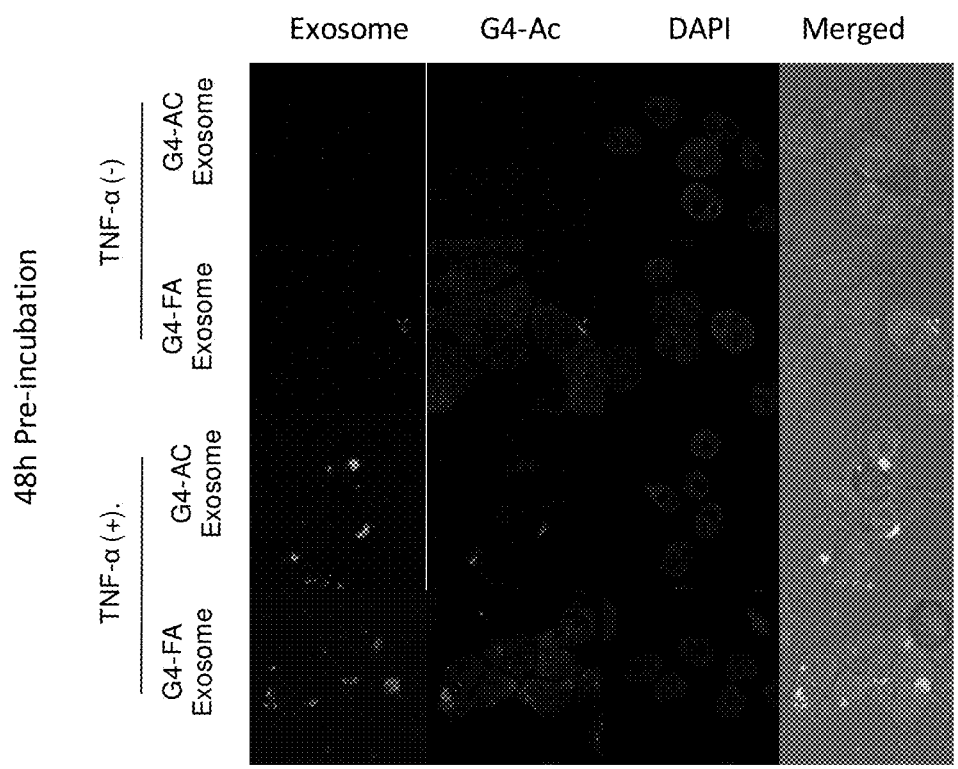
FIG. 17 shows cell interactions of the dendrimer-exosome hybrid NPs at 48 incubation hours.

Cell Interaction of the Dendrimer-Exosome Hybrid NPs at Various Incubation Hours To test the cellular interaction of the hybrid NPs and FA-targeted dendrimers released from the NPs over incubation time, the hybrid NPs were pre-incubated in PBS at 37° C. for 0, 24, and 48 hr to allow the dendrimers to be released from the exosomes. KB cells were cultured in folate-depleted medium at least for 14 days to induce the overexpression of folate receptors. The hybrid NP-containing PBS was then added to folate-overexpressing KB cells (KBFR+) with and without TNF-α pre-treatment. FIGS. 15-17 show fluorescence images from the cells treated with hybrid NPs (15) without, (16) after 24 hr, and (17) after 48 hr pre-incubation. The hybrid NPs selectively interacted with the TNF-α-treated cells regardless of pre-incubation hours. However, the co-localization behaviors of green (exosome) and red (dendrimer) signals were changed depending on the pre-incubation hours. At 0 hr pre-incubation, significant overlapping of the two fluorescence signals was observed, which was substantially decreased with an increase of the pre-incubation hours.

Example 8

Functionalization, Preparation, and Engineering of Biomimetic Hybrid Nanoparticles (BioHNPs)

hMSC-derived exosomes will be used as carriers of multifunctional PAMAM dendrimers that are conjugated with targeting ligands (e.g., peptides), imaging agents (e.g., AlexaFluor®), and drug molecules (e.g., methotrexate). While illustrated for treatment of breast cancer, this delivery system will provide a platform technology that can be applied to many other types of cancer and potentially other diseases. Multivalent interactions can substantially promote recognition of specific cell types by targeted nanocarriers. PAMAM dendrimers mediate multivalent binding, achieving up to 1 million-fold enhancement in binding kinetics compare to its monovalent binding counterpart. However, the drawbacks of PAMAM dendrimers, including short circulation time as well as potential immunogenecity and toxicity, have been well recognized. The hybridization described herein will mitigate, if not eliminate, the concerns while taking advantage of the unique characteristics of dendrimers and exosomes.

Figure 18:
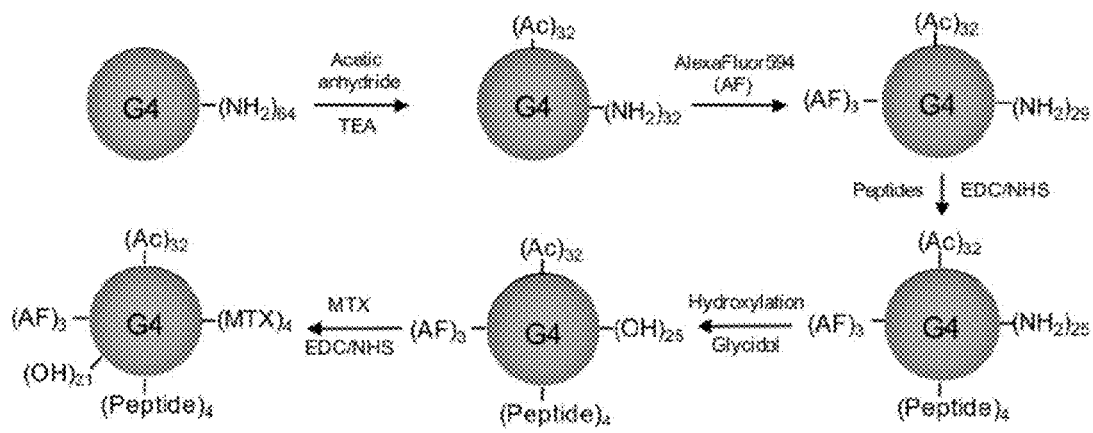
FIG. 18 shows sequential dendrimer functionalization with partial acetylation, conjugation with AlexaFluor594®, peptide conjugation, hydroxylation, and methotrexate conjugation.

Dendrimer functionalization is illustrated in FIG. 18. Various generations (G2-G7) PAMAM dendrimers will be employed for this study. For example, G4 PAMAM dendrimers will be thoroughly purified and partially acetylated, followed by conjugation with N-hydroxysuccinimide (NHS)-terminated AlexaFluor594 (AF). The G4-AF conjugates will then be covalently bound with peptides targeting HER-II receptors overexpressed by many breast cancer cells. The remaining amine groups of the conjugates will then be hydroxylated to allow conjugation with methotrexate (MTX) through ester linkages. Detailed protocols regarding similar chemistries have been previously published. The final G4-AF-pept-MTX will be used for subsequent hybridization with hMSC-dervived exosomes.

HER-II targeting peptides: Four peptide sequences, MLYNPTTYQMDVN (SQ ID NO: 1), VTYNTDT-FESMPN (SEQ ID NO: 2), MYWGDSHWLQYWYE SEQ ID NO: 3), NKFNKGMRGYWGALGGGNGKRGIRGYD (SEQ ID NO: 4), will be tested as targeting ligands. The opposite end of the active site of each peptide will have a cysteine group that will be conjugated with amine groups of dendrimers via succinimidyl 4-(N-maleimidomethyl)cyclohexane-1-carboxylate) (SMCC) linkers. This will allow the proper orientation of the peptides (right-side-out), enabling maximal binding kinetics.

MSC culture and exosome separation: Human mesenchymal stem cells (hMSCs) from Lonza (Walkersville, Md., USA) will be culture expanded following a previously published protocol39 until they reach 70 to 80% confluency. Twenty-four hrs before exosome purification, the culture media (MEM-alpha, fully supplemented) will be replaced with exosome-free media (the same medium but with exosome-free FBS). The cell culture conditioned media will be transferred to new 50 mL conical tubes and centrifuged at 2,000×g for 20 min at 4° C. to remove cells. The supernatants will be centrifuged at 10,000×g for 30 min at 4° C. to remove dead cells and cell debris, followed by another centrifugation at 100,000×g for at least 70 min. The collected pellets will be resuspended in 10 mL of PBS and centrifuged again at 100,000×g for 2 hr to remove soluble proteins. The final pellets (exosomes) will be resuspended in 50 to 200 μL of PBS and stored at −80° C. before use.

Example 9

Selectivity Tests of BioHNPs Against Endothelial Cells and Tumor Cells In Vitro

HUVEC cells and a series of breast cancer cells will be employed. The HER2 positive cells include SKBR3, MDA-MB453, T47D, MCF-7, and the HER2 negative cells include MDA-MB-468, MDA-MB-231, SUM190. These cell lines will be cultured using similar protocols that we previously used. In vitro tests for selectivity and cytotoxicity. We will compare cellular interactions of various groups with the cells before and after TNF-α treatment. Briefly, HUVEC cells and the breast cancer cells ($5 \times 10^3$ cells/well) will be seeded onto an 8-well confocal chamber and incubated at 37° C. under 5% $CO_2$ for 24 hrs before starting any treatment. The cells will be divided into two groups and one of the groups will be treated with TNF-α at 20 ng/mL for 4 hrs. Both TNF-α untreated and treated cells will then be incubated with the all groups (Table 2) at various concentrations (0-25 μg/well) at 37° C. for 2 hrs, followed by a series of analyses using confocal microscopy and FACS. The experimental groups and their corresponding targeting mechanisms are summarized in Table 2.

TABLE 2

| | Experimental design of in vitro experiments | | |
|---|---|---|---|
| No | Core | Shell | Targeting |
| 1 | G(x)-AF | Exosome | VT, Passive |
| 2 | G(x)-AF-peptide | Exosome | VT, Passive, Active |
| 3 | G(x)-AF-MTX | Exosome | VT, Passive, Therapeutic |
| 4 | G(x)-AF-peptide-MTX | Exosome | VT, Passive, Active, Therapeutic |
| 5 | G(x)-AF | Liposome | Passive |
| 6 | G(x)-AF-peptide | Liposome | Passive, Active |
| 7 | G(x)-AF-MTX | Liposome | Passive, Therapeutic |

TABLE 2-continued

Experimental design of in vitro experiments

| No | Core | Shell | Targeting |
|---|---|---|---|
| 8 | G(x)-AF-peptide-MTX | Liposome | Passive, Active, Therapeutic |
| 9 | Free MTX | Exosome | VT, Passive, Therapeutic |
| 10 | Free MTX | Liposome | Passive, Therapeutic |

G(x): Generation X PAMAM dendrimer (X: 2-7),
VT: Vascular targeting

The identical experiments will be performed using dendrimer-liposome hybrid NPs (Groups 5-8 and 10) to investigate the effect of exosomes on the hybrid NP design and function as well. Through this in vitro experimental design, the role of each of the components in BioHNPs will systematically investigated.

Cytotoxicity of MTX to various cell lines will be also compared for Groups 3, 7-10, along with free MTX as a control, using an MTS assay (Promega, Madison, Wis.). Briefly, 3' 103 cells/well will be seeded onto a 96-well plate 24 hrs prior to the addition of the experimental groups at various concentrations, followed by 4 hr incubation at 37° C. The assays will then be performed following the manufacturer's protocol.

The binding strength of the targeting agents (peptides) conjugated with dendrimers and the natural proteins expressed by hMSC-derived exosomes will be separately investigated by Surface Plamon Resonance (SPR) using Biacore™ X. For peptide-dendrimer conjugate binding, HER2 receptors (R&D System, Minneapolis, Minn.) will be immobilized onto the Biacore™ chips. For exosome binding, VCAM-1 and P-selectin (R&D System) will be also immobilized onto separate chips. The subsequent binding assays will be performed according to our previously published protocols. Cell binding of the targeting ligands expressed on exosomes and conjugated on dendrimers will be also measured using AFM, as we previously published.

We expect that BioHNPs will selectively interact with TNF-a activated HUVEC and breast cancer cells, induced by hMSC-dervied exosomes (Groups 1-4 and 9 in Table 2). The dendrimer conjugated with the HER2 receptor targeting peptides, however, will selectively bind to the cells overexpress HER2 receptors (Groups 2, 4, 6, and 8) and demonstrate selective killing of tumor cells (Groups 4 and 8). Furthermore, the binding assays using SPR and AFM will also provide the optimal number of peptides conjugated to dendrimers as well as binding confirmation of exosomes.

Example 10

Biological Assessments of BioHNPs in Terms of Tissue Penetration and Diffusion Using Multicellular Tumor Spheroids Various MCTS models will be prepared using the protocols previously published. In particular, MCTS will be prepared using the liquid overlay method. For example, MCF-7 cells from a confluent T-75 flask will be detached using trypsin-EDTA and resuspended in supplemented RPMI 1640 medium at a concentration of 8,000 cells/mL. Two hundred microliters of cell suspension will be added to each well of a 96-well plate coated with 50 µL of 1.0% agarose in RPMI 1640 completed media. The cells will be incubated on agarose for 5 days to allow the formation of MCTS. After 5 days, 100 µL of the media in each well will be removed, and the MCTS will be treated with the experimental groups summarized in Table 2. Note that dendrimers will be observed by their fluorescence from AF and exosomes will be pre-conjugated with FITC. At the desired treatment times, the MCTS will be visualized using confocal microscopy. Images and fluorescent measurements at the tumor cores will be taken using ImageJ software. The areas defining core and periphery of the MCTS will be dependent upon its size. Just as an example, the fluorescence intensity at the core of the tumor will be defined as the average intensity throughout a circle (600-800 µm$^2$) taken at least 3 points within 15 µm from the centermost point of the MCTS over an area of approximately 50,000 pixels2 and for at least 3 separate MCTS. The average fluorescence over the entire MCTS will be also used to evaluate the overall accumulation of the nanocarriers within the MCTS.

In order to establish a model to measure diffusion coefficients of BioHNP and its components across the extracellular matrix (ECM), the experimental groups will be loaded into collagen type I gels and their permeation will be evaluated using fluorescence recovery after photobleaching (FRAP). For example, to prepare the gels, 270 µL of cold 9.06 mg/mL rat tail type I collagen (Corning, Bedford, Mass.) will be mixed with 6 µL of 50× PBS, 6.21 µL of 1 N NaOH and the appropriate amount of the experimental groups in ddH$_2$O. The mixture was immediately vortexed for 1-2 sec. To form the gel, 100 µL of the mixture will be removed and a drop placed on a cold glass slide and covered using a coverslip. A confocal microscope will be used to photobleach a circular area of 9.347 µm$^2$. The recovery in fluorescence intensity within the circle will be then monitored for 300 sec and fit to a one-phase exponential decay to obtain the half-life of fluorescence recovery, representing the diffusion coefficients of each group.

We expect to observe far more efficient tumor penetration from groups that contain dendrimers, compared to the empty exosomes and liposomes (Groups 9-10). Importantly, those dendrimers with targeting peptides will likely accumulate better and penetrate deeper, compared to the dendrimers without the ligands, considering that the selective binding between the peptide ligands and cell surface receptors will likely provide enhanced opportunities to accumulate and subsequently penetrate, as we reported in the case of amine-terminated dendrimers. The diffusion coefficients, in contrast, may likely give us opposite results. As the dendrimers with ligands will likely go through the MCTS and the ECM model via a transcelluar pathway, the dendrimers without ligands may likely take a paracellualr pathway that facilitates the diffusion efficiency of the macromolecules. It is also expected that the groups with lower generation dendrimers will show higher penetration efficiencies.

Example 11

Evaluating the Blood Circulation Time of the Dendrimer-Exosome Hybrid NPs

To measure the blood circulation time and biodistribution of the nanohybrids, 6-8-week-old BALB/c female mice will be obtained through Laboratory Animal Resources. Each mouse will be anesthetized as previously described prior to receiving a tail vein injection or an IP injection of dendrimers, exosomes, liposomes, or hybrid NPs suspended in 0.2 mL PBS. Entire blood will be collected to measure the amount of the hybrid NPs remaining in the blood. Their organs (liver, lung, heart, spleen, and kidney) will be collected to measure biodistribution of the hybrid NPs at 10 min, 1 h, 3 h, 6 h, 24 h, 48 h, and 72 h postinjection. All the mice will be sacrificed by $CO_2$ at the end of experiment day.

5 compounds using athymic nude mice: (1 negative control×7 time point×5 animals)+(4 test compounds×7 time points×5 animals)=175

TABLE 3

Design of mouse experiment to determine the blood circulation time of the dendrimer-exosome hybrid NPs

| Compound | Animals per Time point | Number | Total number |
|---|---|---|---|
| PBS | 7 | 5 | 70 |
| Dendrimer | 7 | 5 | 70 |
| Liposome | 7 | 5 | 70 |
| Exosome | 7 | 5 | 70 |
| Dendrimer-exosome hybrid NPs | 7 | 5 | 70 |

Example 12

Evaluating the Biodistribution, Tumor Accumulation, and Therapeutic Effect of the Dendrimer-Exosome Hybrid NPs in Mice 6-8-week-old BALB/c female athymic nude mice will be obtained through Laboratory Animal Resources. FR+ cells, such as KB cells, will be suspended in 0.2 mL PBS and injected subcutaneously (day 0) with aseptic techniques (using a 30 g needle/1 ml disposable syringe) into the right flank of each mouse. The mice will be anesthetized with an IP injection of Ketamine/Xylazine (50 mg/kg and 5 mg/kg, respectively) prior to each injection. The tumors will be allowed to grow for 2 weeks until reaching ~50-100 mm³ in volume. Tumor growth will be monitored by measuring two axes and calculating its volume. The experiments will be terminated after 4 weeks and mice will be sacrificed by $CO_2$ asphyxiation.

Two weeks after tumor implantation, each mouse will be anesthetized as previously described prior to receiving a tail vein injection or an IP injection of dendrimers, exosomes, liposomes, or hybrid nanoparticles (NPs) suspended in 0.2 mL PBS. Prior to the injection of NPs, TNF-alpha may administered via I.T or I.V injection. At 5 minutes, 2, 4 and 24 hours, 3, 5, and 7 days postinjection, the animals will be monitored to track tumor accumulation of hybrid NPs using the In Vivo Imaging System (IVIS) spectrum (Perkin Elmer). At the end of the experiment, their entire blood will be collected to measure the amount of the hybrid NPs remaining in the blood. Their organs (liver, lung, heart, spleen, kidney, and tumor) will be collected to measure bio-distribution of the hybrid NPs. Samples of organs will be taken and immediately imaged using IVIS and frozen for sectioning.

Mice will be monitored daily for 4 weeks after tumor cell inoculation for any toxicities associated with either the tumor or nanoparticle treatments. The animals will be weighed weekly as an indication of the adverse effects and tumors measured weekly. Mice will be sacrificed by $CO_2$ before the scheduled date if the mouse becomes moribund. Tumor volumes will be calculated using the following formula: V=0.52×length [L]×width [w]×height [H]. All remaining animals will be sacrificed by $CO_2$ asphyxiation at 42 days post inoculation.

14 compounds using athymic nude mice: (1 negative control×5 animals)+(13 test compounds×5 animals)=70

TABLE 4

Experimental Design for evaluating the biodistribution, tumor accumulation, and therapeutic effect of the dendrimer-exosome hybrid NPs in mice

| Compound | Group | Number |
|---|---|---|
| PBS | Negative control | 5 |
| Dendrimers* | Test compound | 5 |
| MTX | Test compound | 5 |
| Dendrimer-FA conjugates | Test compound | 5 |
| Dendrimer-FA-MTX conjugates | Test compound | 5 |
| Exosomes | Test compound | 5 |
| Liposomes | Test compound | 5 |
| Dendrimer/Exosome hybrids | Test compound | 5 |
| Dendrimer-FA/Exosome hybrids | Test compound | 5 |
| Dendrimer-FA-MTX/Exosome hybrids | Test compound | 5 |
| Dendrimer/liposome hybrids | Test compound | 5 |
| Dendrimer/liposome hybrids | Test compound | 5 |
| Dendrimer-FA/Liposome hybrids | Test compound | 5 |
| Dendrimer-FA-MTX/Liposome hybrids | Test compound | 5 |

*Dendrimer: PAMAM dendrimer, generation 2, 4, and 7, Acetylated dendrimer, Caboxylated dendrimer, and hydroxylated dendrimer. All dendrimers will be labeled with fluorescence dyes (Rhodamine, FITC, Alexa Fluor ® 488, Alexa Fluor ® 594, Alexa Fluor ® 647, and Alexa Fluor ® 680).

Figure 19:
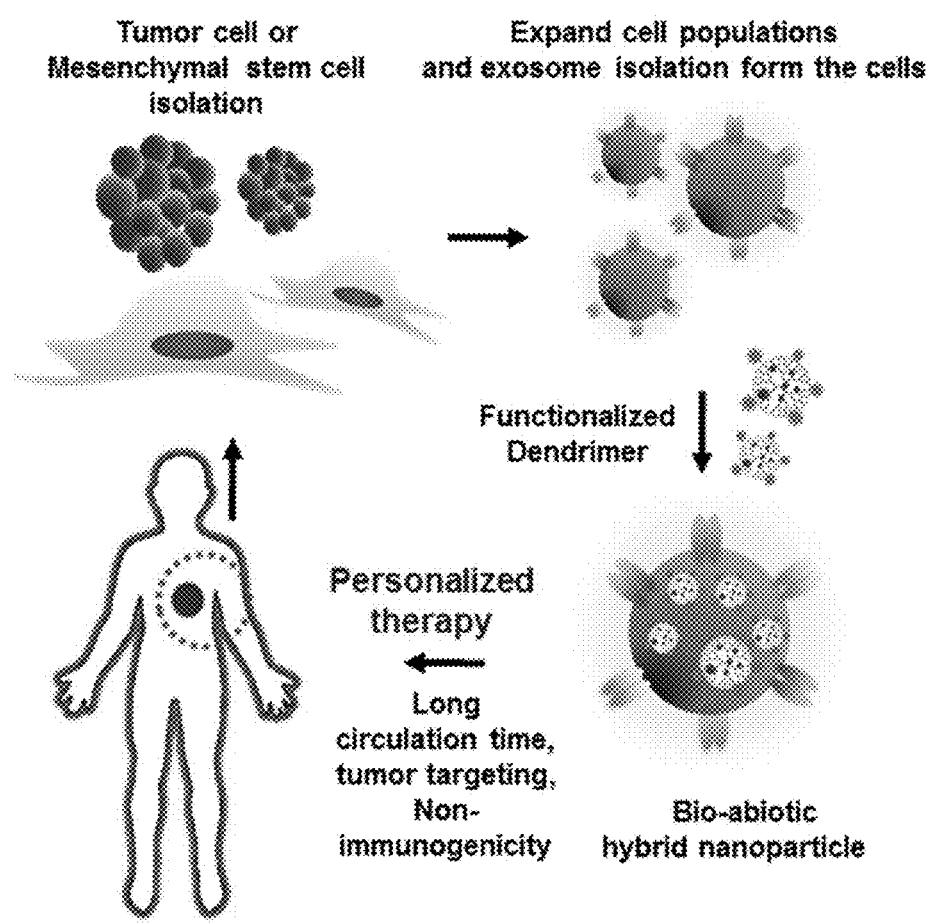
FIG. 19 is a schematic of a personalized medicine approach using the bio-abiotic hybrid nanoparticles.

The integration of biotic/abiotic nano-scale materials, multiple targeting mechanisms, and therapeutic drugs within a single hybrid NP system will allow for significantly enhanced targeting efficacy with minimal concern of immunogenicity and toxicities, ultimately achieving truly personalized medicine, as illustrated in FIG. 19. The significance of the proposed work is two-fold: 1) enhanced targeting efficacy by harnessing four mechanisms of passive and vascular targeting, followed by efficient tumor penetration and active targeting in a sequentially controlled manner and 2) the use of biological vesicles (exosomes) that will be derived from individual patients, which will ultimately allow personalized medicine. Upon successful completion of this proposed study, we will have a highly effective, transformative biotic/abiotic hybrid NP platform system that potentially offers an excellent theragnostic tool not only for breast cancer but also for other cancers and other debilitating diseases.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A hybrid nanoparticle for targeting inflamed epithelia, comprising:
   an exosome loaded with one or more PAMAM dendrimers,
   wherein the exosome is isolated from human mesenchymal stem cells, wherein the exosome expresses the membrane proteins VLA-4, CD162, CXCR4, or a combination thereof, and wherein the exosome also expresses the exosome markers CD9, CD63, and CD81; and
   wherein the PAMAM dendrimer comprises a tumor-targeting agent and an anti-tumor agent, wherein the agents are bound via multivalent covalent interactions with the PAMAM dendrimer, and wherein the hybrid nanoparticle specifically targets inflamed epithelia.

2. The hybrid nanoparticle of claim 1, wherein the mesenchymal stem cell is from umbilical cord, cord blood, bone marrow, fat, muscle, nerve, skin, amnion, or placenta.

3. The hybrid nanoparticle of claim 1, wherein the dendrimer is associated with a therapeutic, a prophylactic, or a diagnostic agent.

4. The hybrid nanoparticle of claim 1, wherein the anti-tumor agent is a chemotherapeutic agent.

5. The hybrid nanoparticle of claim 3, wherein the therapeutic agent is a therapeutic nucleic acid.

6. The hybrid nanoparticle of claim 1, wherein the tumor-targeting agent is a tumor-targeting peptide.

7. The hybrid nanoparticle of claim 3, wherein the diagnostic agent is an imaging agent.

8. A pharmaceutical composition comprising the hybrid nanoparticle of claim 1.

9. A method of treating a human subject, comprising administering to the human subject the hybrid nanoparticles of claim 5.

* * * * *